US010458920B2

(12) United States Patent
Planas et al.

(10) Patent No.: US 10,458,920 B2
(45) Date of Patent: Oct. 29, 2019

(54) SYSTEMS AND METHODS FOR ENSURING PROPER TUBING INSTALLATION FOR FLUID PROCESSING SYSTEMS

(71) Applicant: Fenwal, Inc., Lake Zurich, IL (US)

(72) Inventors: Samantha M. Planas, Wauconda, IL (US); Amit J. Patel, Algonquin, IL (US); Melissa A. Thill, Kenosha, WI (US); Nicholas Reimold, Evanston, IL (US); Courtney Moore, San Diego, CA (US); William Henry Cork, III, Mettawa, IL (US)

(73) Assignee: Fenwal, Inc., Lake Zurich, IL (US)

( * ) Notice: Subject to any disclaimer, the term of this patent is extended or adjusted under 35 U.S.C. 154(b) by 619 days.

(21) Appl. No.: 14/827,811

(22) Filed: Aug. 17, 2015

(65) Prior Publication Data

US 2017/0052124 A1    Feb. 23, 2017

(51) Int. Cl.
*G01N 21/85* (2006.01)
*A61M 1/36* (2006.01)

(52) U.S. Cl.
CPC ............. *G01N 21/85* (2013.01); *A61M 1/367* (2013.01); *A61M 2202/0413* (2013.01); *A61M 2205/3306* (2013.01)

(58) Field of Classification Search
CPC ..... G01N 21/85; A61M 1/3496; A61M 1/367; A61M 1/3693; A61M 1/36;

(Continued)

(56) References Cited

U.S. PATENT DOCUMENTS 3,935,876 A    2/1976 Massie et al.
4,673,927 A    6/1987 Cianciavicchla et al.
(Continued)

FOREIGN PATENT DOCUMENTS

EP              0522527       1/1993
WO    WO 2012/006425 A2    1/2012
WO    WO 2012/125457       9/2012

OTHER PUBLICATIONS

Extended European Search Report for EP 16181233.4-1651, dated Jan. 13, 2017.

*Primary Examiner* — Robert Clemente
*Assistant Examiner* — Akash K Varma
(74) *Attorney, Agent, or Firm* — Cook Alex Ltd.

(57) ABSTRACT

A fluid separation system is provided for separating a plasma-containing fluid into separated plasma and a concentrated fluid. The system cooperates with a fluid flow circuit including a fluid separation chamber and a plasma outlet line associated therewith for removing separated plasma from the fluid separation chamber. The system includes an optical sensor assembly that receives a portion of the plasma outlet line when the fluid flow circuit has been associated with the fluid separation system. To ensure proper installation of the plasma outlet line, the optical sensor assembly compares light received by its light detector to a baseline value, which is indicative of the amount of light received by the light detector before the plasma outlet line has been installed. The amount of received light being equal to or less than a selected percentage of the baseline value indicates that the plasma outlet line has been properly installed.

20 Claims, 7 Drawing Sheets

(58) Field of Classification Search
CPC ...... A61M 2202/0413; A61M 2205/14; A61M 2205/3306; A61M 2205/3313
USPC .......................................................... 210/94
See application file for complete search history.

(56) References Cited

U.S. PATENT DOCUMENTS

| | | |
|---|---|---|
| 5,194,145 A | 3/1993 | Schoendorfer |
| 5,234,608 A | 8/1993 | Duff |
| 6,531,708 B1 | 3/2003 | Malmstrom et al. |
| 6,750,468 B2 | 6/2004 | Malmstrom et al. |
| 7,789,245 B2 | 9/2010 | Westberg et al. |
| 8,708,950 B2 * | 4/2014 | Scarpaci ............... G01V 8/20 250/216 |
| 2003/0214412 A1 | 11/2003 | Ho et al. |
| 2009/0012455 A1 | 1/2009 | Childers et al. |
| 2010/0175483 A1 | 7/2010 | O'Mahony et al. |
| 2012/0123322 A1 | 5/2012 | Scarpaci et al. |
| 2012/0289928 A1 | 11/2012 | Wright et al. |
| 2014/0045668 A1 * | 2/2014 | Case ................... A61M 1/3696 494/1 |
| 2015/0202383 A1 * | 7/2015 | Juretich ............ A61M 5/14232 604/111 |

* cited by examiner

SYSTEMS AND METHODS FOR ENSURING PROPER TUBING INSTALLATION FOR FLUID PROCESSING SYSTEMS

BACKGROUND

Field of the Disclosure

The present disclosure relates to fluid separation systems and methods. More particularly, the present disclosure relates to systems and methods for ensuring that tubing has been properly installed onto a fluid processing device.

Description of Related Art

Various blood processing systems now make it possible to collect particular blood constituents, instead of whole blood, from a blood source such as, but not limited to, a container of previously collected blood or other living or non-living source. Typically, in such systems, whole blood is drawn from a blood source, the particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents (e.g., red cells, platelets, and plasma) through centrifugation, such as in the AMICUS® separator from Fenwal, Inc. of Lake Zurich, Ill., or other centrifugal separation devices, or a spinning membrane-type separator, such as the AUTOPHERESIS-C® and AURORA® devices from Fenwal, Inc.

Typically, a disposable fluid flow circuit is provided for use in combination with a durable, reusable blood processing system. The fluid flow circuit includes a plurality of components (e.g., fluid storage bags and separation chambers) connected by tubing lines, which must be properly installed onto the blood processing system. Known systems may include an alert or alarm system that is programmed to generate an alert or alarm when there is a problem with the blood processing system or fluid flow circuit (e.g., if it has been improperly installed onto the blood processing system), but there remains room for improvement in the ways in which improperly installed tubing may be identified.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid processing system is configured to cooperate with a fluid flow circuit. An optical sensor assembly of the system is configured to receive a portion of the fluid flow circuit and includes a light source and a light detector. The light source emits a light, with the light detector receiving a portion of the light and producing an output that is indicative of the amount of received light. A controller of the system is programmed to receive the output from the light detector and determine whether the portion of the fluid flow circuit is properly received by the optical sensor assembly. The controller makes this determination by comparing the output from the light detector to a baseline value that is indicative of the amount of light from the light source that is received by the light detector when the optical sensor assembly is empty (i.e., in the absence of the portion of the fluid flow circuit). If the output from the light detector is equal to or less than a selected percentage of the baseline value, then the controller has determined that the portion of the fluid flow circuit is properly received by the optical sensor assembly.

In another aspect, a method is provided for determining whether a portion of a fluid flow circuit is properly associated with a fluid processing system. The method includes emitting a light through a space configured to receive a portion of a fluid flow circuit. At least a portion of the light is received and the amount of received light is compared to a baseline value, which is indicative of the amount of light received in the absence of the portion of the fluid flow circuit. If the amount of received light is equal to or less than a selected percentage of the baseline value, then it has been determined that the portion of the fluid flow circuit is properly associated with the fluid processing system.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

According to an aspect of the present disclosure, a durable or reusable fluid processing system is used in combination with a separate fluid flow circuit (which may be disposable) to process or treat a fluid. In one embodiment, which will be described in greater detail herein, the fluid processing system is provided as a fluid separation system that is configured to separate biological fluid into two or more components (e.g., by separating blood or another plasma-containing bodily fluid into separated plasma and a concentrated fluid). While the systems and methods described herein may have particular utility in connection with a blood separation device and its use in separating plasma from other blood components, it should be understood that the present disclosure is not limited to any particular fluid treatment procedure or treatment of any particular fluid.

Figure 1:
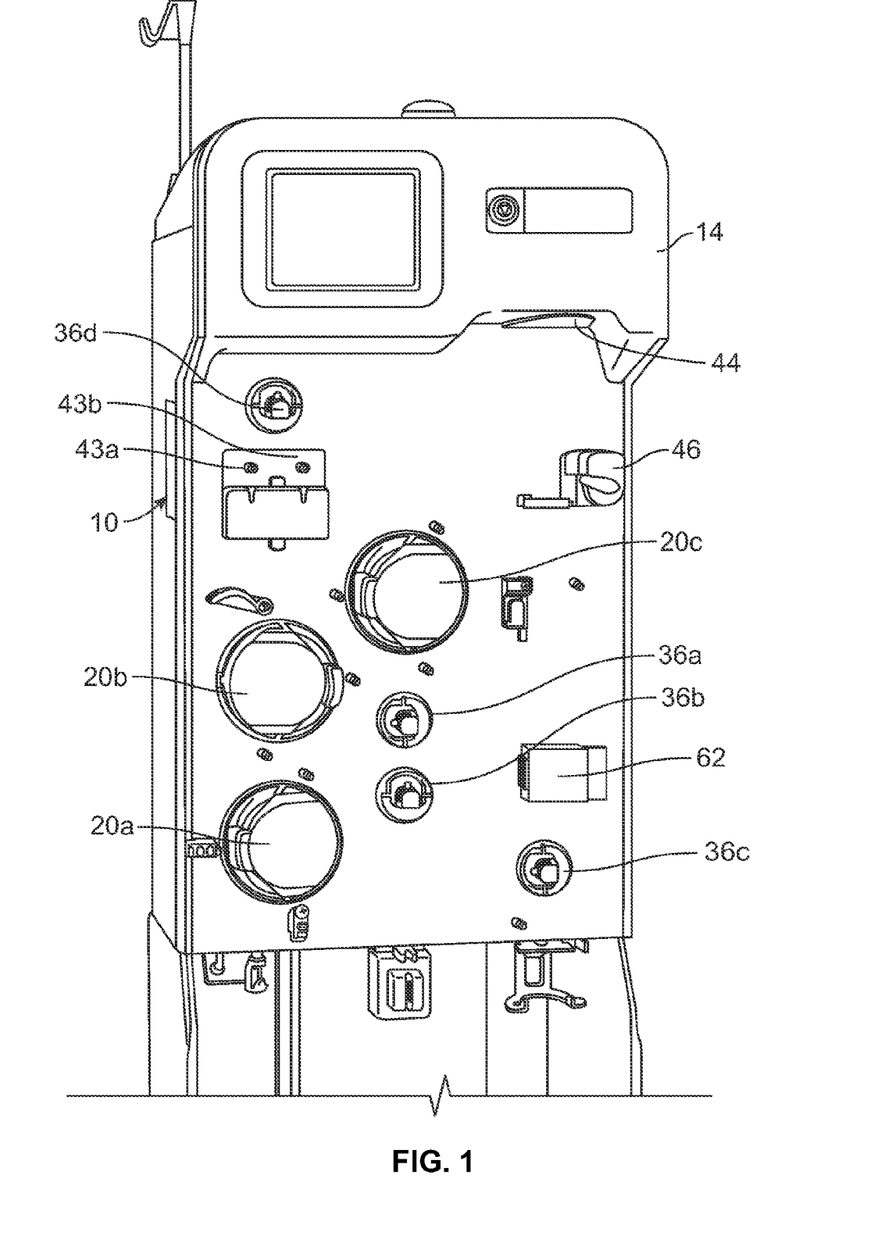
FIG. 1 is a front perspective view of an exemplary fluid processing system according to an aspect of the present disclosure.
Figure 2:
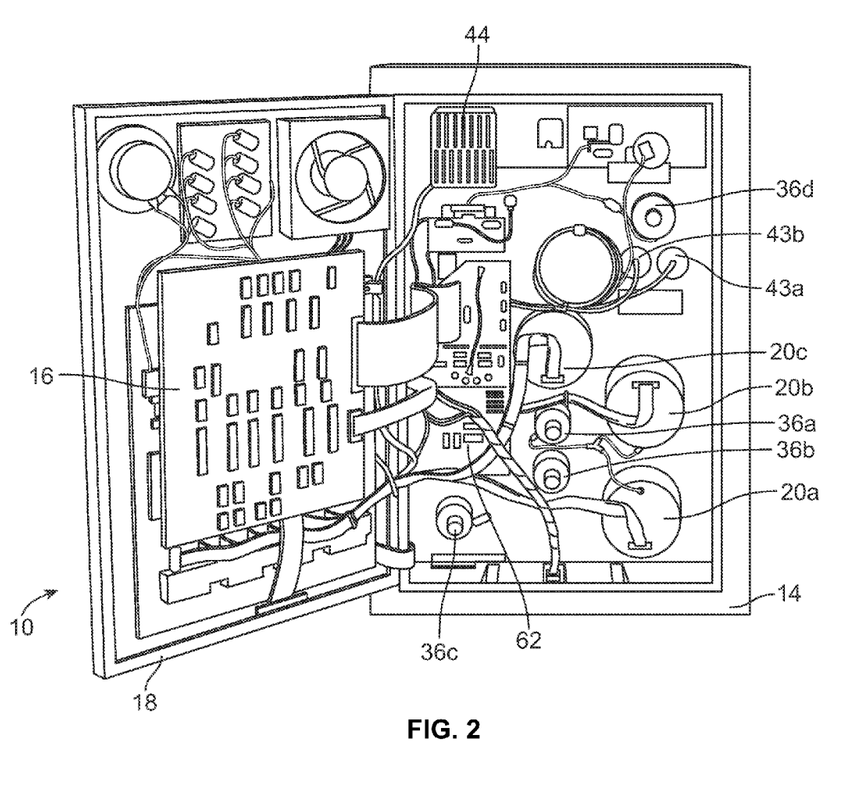
FIG. 2 is a rear perspective view of the fluid processing system of FIG. 1, with a rear door thereof in an open position.
Figure 3:
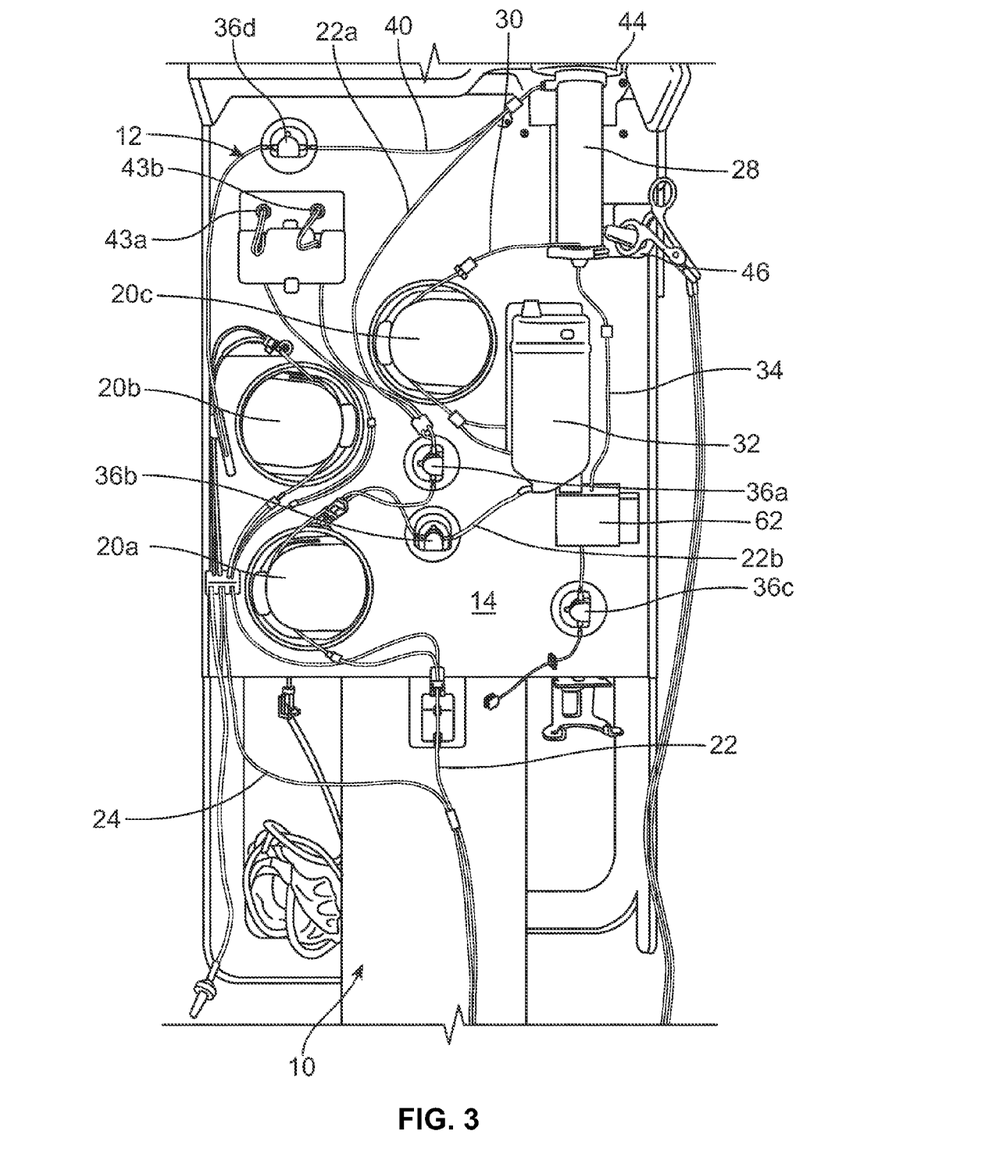
FIG. 3 is a front perspective view of the fluid processing system of FIG. 1, with a fluid flow circuit associated therewith.

FIGS. 1 and 2 illustrate an exemplary fluid processing or separation system 10, while FIG. 3 illustrates an exemplary fluid flow circuit 12 mounted onto the fluid processing system 10, but it should be understood that the illustrated fluid processing system 10 and fluid flow circuit 12 are merely exemplary of such systems and circuits and that differently configured fluid processing systems and fluid flow circuits may be provided without departing from the scope of the present disclosure.

The system 10 of FIG. 1 is configured for processing whole blood, but it may be used to process any other plasma-containing fluid to separate plasma from concentrated fluid (which may be red cell concentrate or packed red cells when the plasma-containing fluid constitutes whole blood). The plasma-containing fluid may come from any fluid source, which may include a living donor or patient (e.g., a human blood donor) or a non-living source (e.g., a blood bag or fluid container).

Figure 5:
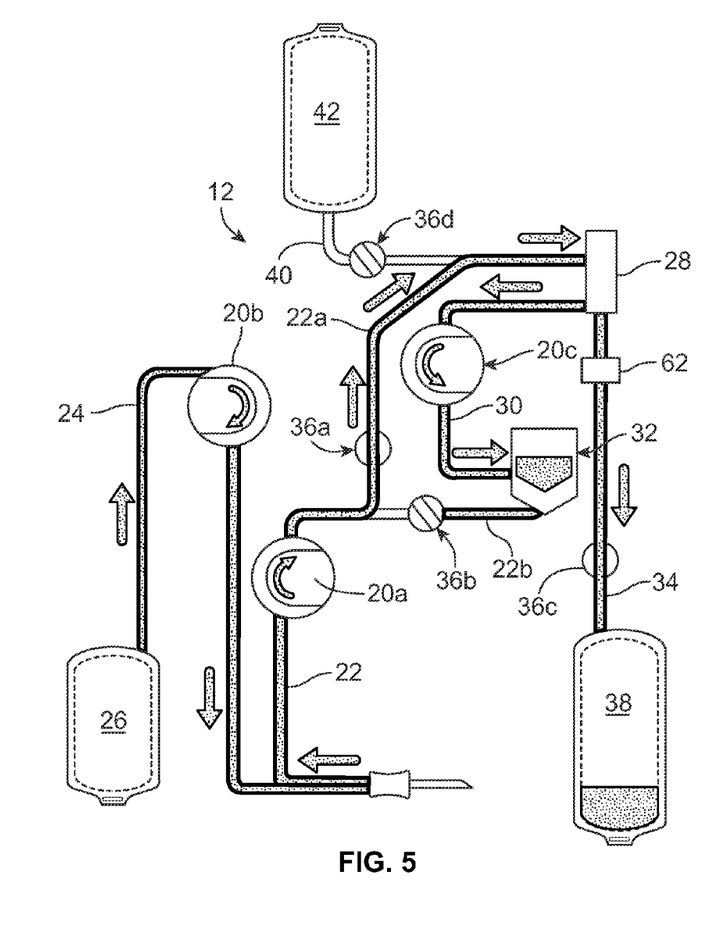
FIG. 5 is a schematic view of the fluid flow circuit and fluid processing system of FIG. 3, in a fluid draw mode.
Figure 6:
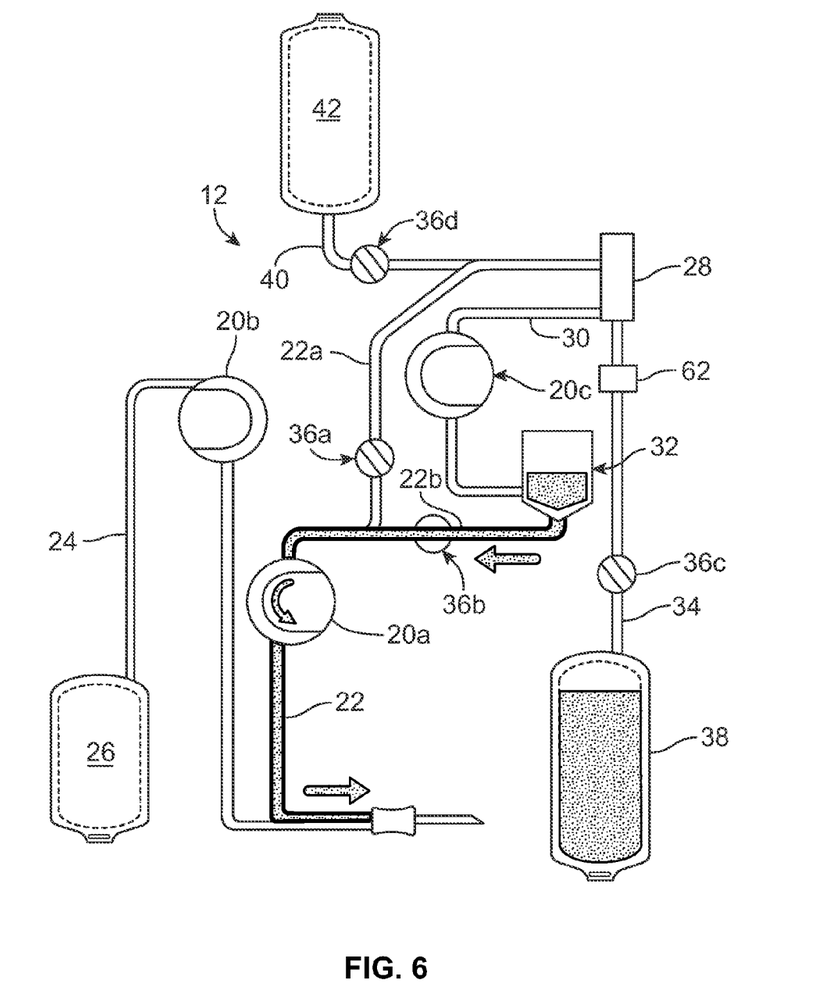
FIG. 6 is a schematic view of the fluid flow circuit and fluid processing system of FIG. 3, in a fluid return mode.

The illustrated system 10 includes a cabinet or housing 14, with several components positioned outside of the cabinet 14 (e.g., associated with a front wall or surface or panel of the cabinet 14) and additional components (including a central processing unit or controller 16) and interconnects positioned inside of the cabinet 14, which may be accessed by opening a rear door 18 of the system 10, as shown in FIG. 2. It should be understood that the illustrated system components and the location of the components is merely exemplary, and that additional or different components and different component arrangements may be incorporated into the system without departing from the scope of the present disclosure. Among the system components positioned on the outside of the cabinet 14, one or more pumps or pump stations 20a-20c may be provided, with the pumps 20a-20c configured to accommodate tubing lines of the fluid flow circuit 12. One of the pumps 20a may be provided as a source/recipient access pump, which may be associated with a source/recipient access line 22 of the fluid flow circuit 12 and operates to draw fluid from a fluid source (FIG. 5) and to return fluid to a fluid recipient (FIG. 6). Another one of the pumps 20b may be provided as an anticoagulant pump, which may be associated with an anticoagulant line 24 of the fluid flow circuit 12 and operates to add anticoagulant from an anticoagulant source or container 26 of the fluid flow circuit 12 (FIG. 5) to fluid drawn from the fluid source in the source/recipient access line 22 before the fluid enters into a fluid separation module or chamber 28 of the fluid flow circuit 12. A third pump 20c may be provided as a concentrated fluid pump, which may be associated with a concentrated fluid outlet line 30 and operates to draw concentrated fluid from the fluid separation chamber 28 and direct it into a concentrated fluid reservoir 32 after the plasma-containing fluid has been separated into a concentrated fluid and separated plasma in the fluid separation chamber 28.

In the illustrated embodiment, the pumps 20a-20c are peristaltic pumps, but it is within the scope of the present disclosure for differently configured pumps, such as diaphragm or other pumps, to be provided. Furthermore, additional or alternative pumps may be provided without departing from the scope of the present disclosure. For example, a pump may be associated with a plasma outlet line 34 of the fluid flow circuit 12 to draw separated plasma from the fluid separation chamber 28 after the plasma-containing fluid has been separated into a concentrated fluid and separated plasma. Also, as will be described in greater detail herein, the illustrated embodiment employs a single fluid flow tubing or flow path for both drawing fluid from a source and flowing or returning it to a recipient, which are carried out intermittently. The system 10 could employ separate draw and return flow paths or tubes without departing from the scope of the present disclosure.

In addition to the pumps 20a-20c, the external components of the system 10 may include one or more clamps or valves 36a-36d associated with the tubing lines of the fluid flow circuit 12. The clamps or valves 36a-36d may be variously configured and operate to selectively allow or prevent fluid flow through the associated tubing line. In the illustrated embodiment, one clamp or valve 36a may be provided as a fluid source/recipient clamp, which may be associated with a draw branch 22a of the source/recipient access line 22 of the fluid flow circuit 12 to allow (FIG. 5) or prevent (FIG. 6) the flow of fluid through the draw branch 22a of the source/recipient access line 22. Another one of the clamps or valves 36b may be provided as a reinfusion clamp or valve, which may be associated with a reinfusion branch 22b of the source/recipient access line 22 downstream of a concentrated fluid reservoir 32 of the fluid flow circuit 12 to allow (FIG. 6) or prevent (FIG. 5) the flow of concentrated fluid through the reinfusion branch 22b. A third clamp or valve 36c may be provided as a plasma clamp or valve, which may be associated with the plasma outlet line 34 to allow (FIG. 5) or prevent (FIG. 6) the flow of separated plasma through the plasma outlet line 34 and into a separated plasma container 38. A fourth clamp or valve 36d may be provided as a replacement fluid clamp or valve, which may be associated with a replacement fluid line 40 of the fluid flow circuit 12 to allow or prevent the flow of a replacement fluid out of a replacement fluid source 42 (e.g., a bag or container at least partially filled with saline). Additional or alternative clamps or valves may also be provided without departing from the scope of the present disclosure.

The illustrated system 10 further includes one or more pressure sensors 43a and 43b that may be associated with the fluid flow circuit 12 to monitor the pressure within one or more of the tubing lines of the fluid flow circuit 12 during operation of the pumps 20a-20c and clamps or valves 36a-36d. In one embodiment, one pressure sensor 43a may be associated with a tubing line that draws fluid from a fluid source and/or directs processed fluid to a fluid recipient, while the other pressure sensor 43b may be associated with a tubing line that directs fluid into or out of the fluid separation chamber 28 to assess the pressure within the fluid separation chamber 28, but the pressure sensors 43a and 43b may also be associated with other tubing lines without departing from the scope of the present disclosure. The pressure sensors 43a and 43b may send signals to the system controller 16 that are indicative of the pressure within the tubing line or lines being monitored by the pressure sensor 43a, 43b. If the controller 16 determines that an improper pressure is present within the fluid flow circuit 12 (e.g., a high pressure due to an occlusion of one of the tubing lines), then the controller 16 may instruct one or more of the pumps 20a-20c and/or one or more of the clamps or valves 36a-36d to act so as to alleviate the improper pressure condition (e.g., by reversing the direction of operation of one of the pumps 20a-20c and/or opening or closing one of the clamps or valves 36a-36d). Additional or alternative pressure sensors may also be provided without departing from the scope of the present disclosure.

The system 10 may also include a separation actuator 44 that interacts with a portion of the fluid separation chamber 28 to operate the fluid separation chamber 28. A chamber lock 46 may also be provided to hold the fluid separation chamber 28 in place with respect to the system cabinet 14 and in engagement with the separation actuator 44. The configuration and operation of the separation actuator 44 depends upon the configuration of the fluid separation chamber 28. In the illustrated embodiment, the fluid separation chamber 28 is provided as a spinning membrane-type separator, such as a separator of the type described in greater detail in U.S. Pat. Nos. 5,194,145 and 5,234,608 or in PCT Patent Application Publication No. WO 2012/125457 A1, all of which are hereby incorporated herein by reference. If provided as a spinning membrane-type separator, the fluid separation chamber 28 may include a tubular housing 48 (FIG. 4), with a microporous membrane 50 positioned therein. An inlet 52 allows a plasma-containing fluid to enter into the housing 48 (via the draw branch 22a of the source/recipient access line 22), while a side outlet 54 allows concentrated fluid to exit the housing 48 (via the concentrated fluid outlet line 30) and a bottom outlet 56 allows separated plasma to exit the housing 48 (via the plasma outlet line 34) after the plasma-containing fluid has been separated into concentrated fluid and plasma.

Figure 4:
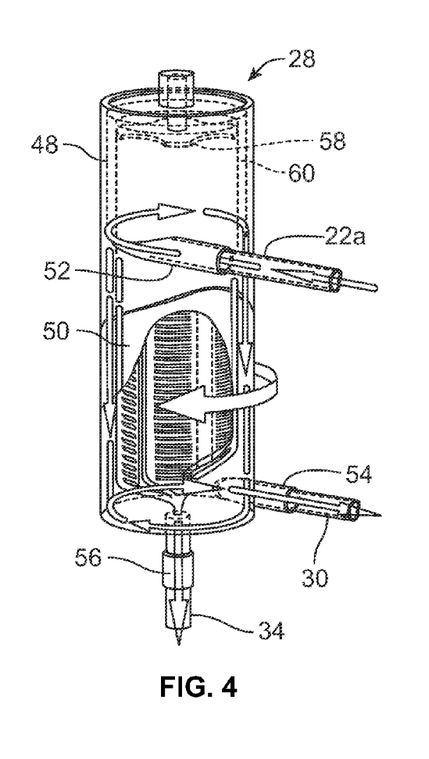
FIG. 4 is a front perspective view of a fluid separation chamber of the fluid flow circuit of FIG. 3, with a portion thereof broken away for illustrative purposes.

In the illustrated embodiment, the separation actuator 44 is provided as a driver that is magnetically coupled to a rotor 58 on which the membrane 50 is mounted, with the separation actuator 44 causing the rotor 58 and membrane 50 to rotate about the central axis of the housing 48. The rotating rotor 58 and membrane 50 create Taylor vortices within a gap 60 between the housing 48 and the membrane 50, which tend to transport the concentrated fluid (which may be cellular blood components) away from the membrane 50 to exit the fluid separation chamber 28 via the side outlet 54, while the separated plasma passes through the membrane 50 toward the central axis of the housing 48 to exit the fluid separation chamber 28 via the bottom outlet 56. It should be understood that the present disclosure is not limited to a particular fluid separation chamber and that the illustrated and described fluid separation chamber 28 is merely exemplary. For example, in other embodiments, a centrifugal device that separates fluid components based on density, rather than size, may be employed to separate a plasma-containing fluid into plasma and a concentrated fluid.

The system 10 further includes a hemoglobin detector or optical sensor assembly 62 associated with the plasma outlet line 34 when the fluid flow circuit 12 has been installed on the system 10. The optical sensor assembly 62 is used to determine the concentration of free plasma hemoglobin in the separated plasma flowing through the plasma outlet line 34 (and may also detect other irregularities in the plasma outlet line 34, such as red blood cells, lipids, and air bubbles) and may be variously configured. The optical sensor assembly 62 may also be used to determine whether the plasma outlet line 34 has been properly installed prior to initiation of a fluid separation procedure, as will be described in greater detail.

Figure 8:
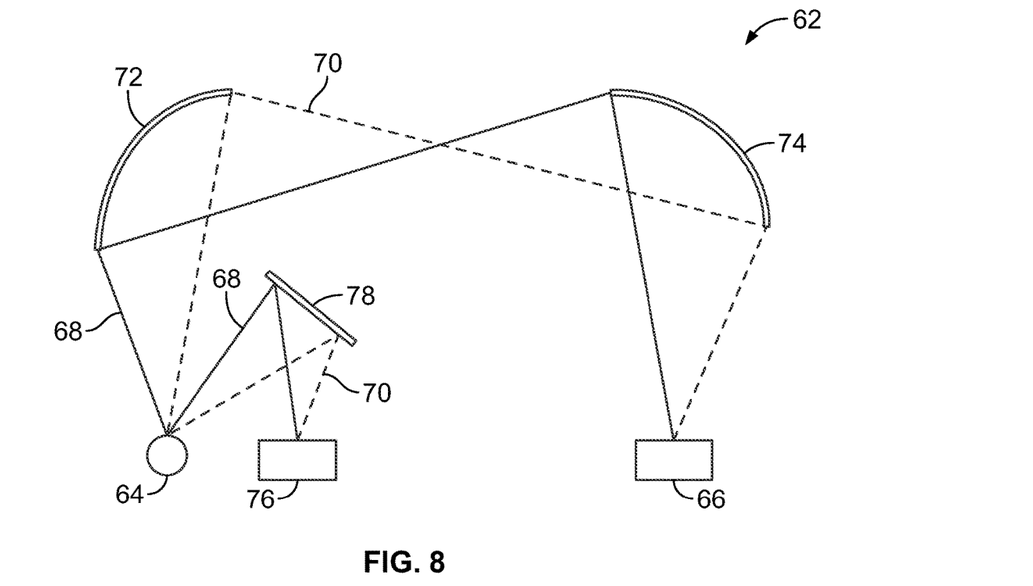
FIG. 8 is a schematic view of an optical sensor assembly of the fluid processing system of FIG. 1.
Figure 9:
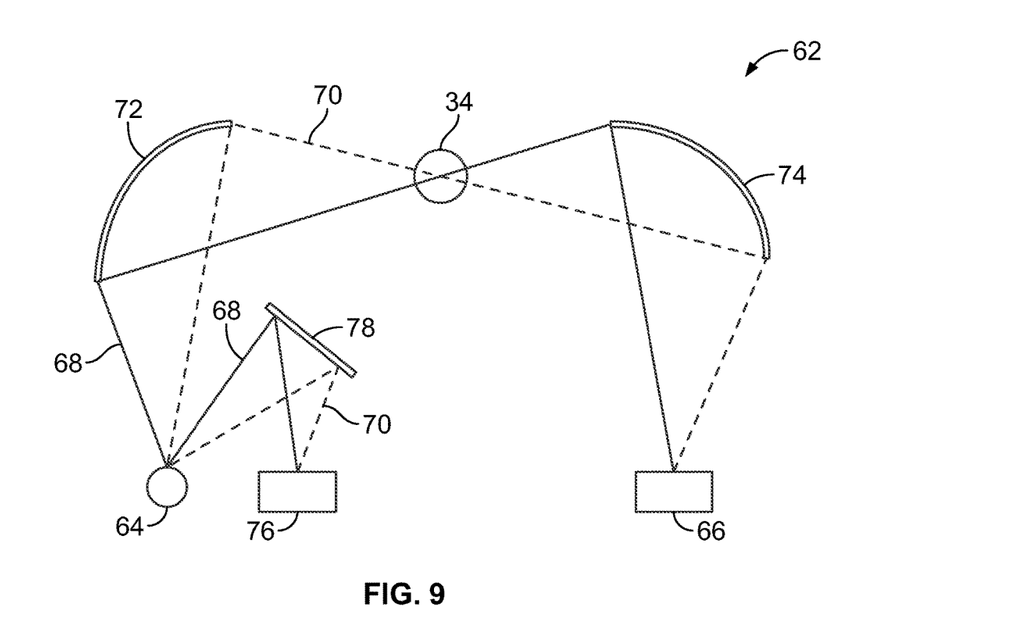
FIG. 9 is a schematic view of the optical sensor assembly of FIG. 8, receiving a portion of a plasma outlet line of the fluid flow circuit of FIG. 3.

In one embodiment, which is shown in FIGS. 8 and 9, the optical sensor assembly 62 includes a light source 64 and a light detector 66. The light source 64 is configured to emit light 68, 70, with at least a portion of the light 68, 70 being received by the light detector 66. The light 68, 70 is transmitted through a portion of the plasma outlet line 34 (FIG. 9) that is received by the optical sensor assembly 62 when the fluid flow circuit 12 has been associated with the system 10. In the illustrated embodiment, a portion of the light 68, 70 is directed to the light detector 66 by a pair of spherical mirrors 72 and 74 (which are configured to receive a portion of the plasma outlet line 34 therebetween), but it is also within the scope of the present disclosure for differently shaped mirrors to be provided or for the light 68, 70 to be directed to the light detector 66 using only one mirror or more than two mirrors. It is also within the scope of the present disclosure for the light 68, 70 emitted by the light source 64 to reach the light detector 66 without being redirected by a mirror or comparable light-directing device or surface.

FIGS. 8 and 9 show two light rays 68 (illustrated as a solid line) and 70 (illustrated as a broken line) being emitted by the light source 64 and received by the light detector 66. In one embodiment, the light rays 68 and 70 represent light of different wavelengths that may be emitted by the light source 64, although it is also within the scope of the present disclosure for only one type of light ray to be emitted by the light source 64. If emitting lights of different wavelengths, the light source 64 may be either a single component (e.g., a light-emitting diode or other light emitter) or a pair of components (e.g., two light-emitting diodes or other light emitters). In one embodiment, the light source 64 is configured to emit red light 68 (which may have a peak wavelength of 635 nm and a dominant wavelength of approximately 626 nm) and green light 70 (which may have a peak wavelength of 568 nm and a dominant wavelength of approximately 570 nm), with the light source 64 comprising a bi-color light-emitting diode that can alternatively emit only red light 68 and only green light 70. The use of red and green light 68 and 70 may be advantageous due to their use in detecting free plasma hemoglobin within the plasma outlet line 34, as will be described in greater detail, but it is also within the scope of the present disclosure for other types of light to be emitted by the light source 64.

The light detector 66 may be variously configured without departing from the scope of the present disclosure. For example, the light detector 66 may be configured as a phototransistor, an infrared light detector, a photodiode, a photovoltaic cell, or a combination thereof, as well as any other suitable type of light detector. It is also within the scope of the present disclosure for the optical sensor assembly 62 to include two or more light detectors, such as one light detector configured to detect one type of light and another light detector configured to detect a second type of light. Regardless of the particular configuration, each light detector 66 is associated with the controller 16 and configured to produce an output that is indicative of the amount of light it has received, which output may be used by the controller 16 for a number of different purposes, as will be described.

In addition to the light source 64 and light detector 66, the optical sensor assembly 62 may also include additional components without departing from the scope of the present disclosure. For example, the optical sensor assembly 62 may include a cover or housing that blocks ambient light from reaching the detector(s) 66. The optical sensor assembly 62 may also include a reference detector 76, which receives a portion of the light 68, 70 from the light source 64 (either directly or after the light has been redirected by a mirror 78 or the like). In one embodiment, the reference detector 76 is identical to the light detector 66 in structure and functionality, but it is also within the scope of the present disclosure for the light detector 66 and 76 to be differently configured and/or to function differently. The reference detector 76 is oriented to receive light 68, 70 that has not passed through the plasma outlet line 34, but instead is configured to produce an output to the controller 16 that is indicative of the amount of light 68, 70 emitted by the light source 64, which may decrease over time.

Separated plasma passing through the plasma outlet line 34 is relatively clear and uncolored in the absence of free plasma hemoglobin (as well as red blood cells, lipids, and other blood components), such that substantially all of the light 68, 70 emitted into the plasma outlet line 34 should exit the plasma outlet line 34 and be received by the light detector 66. Any loss of light caused by the presence of the tubing itself may be taken into account to isolate the effect of the plasma in the tubing when light passes therethrough. If the plasma outlet line 34 contains an optically dense, but colorless fluid, then the transmissivity of both red and green light 68 and 70 through the plasma outlet line 34 will decrease to similar degrees. This is most likely to occur if the plasma is highly lipemic, but may also occur when an air bubble is present in the separated plasma or if the plasma outlet line 34 is improperly aligned within the optical sensor assembly 62. If free plasma hemoglobin is present in the separated plasma, then the transmissivity of green light 70 through the plasma outlet line 34 will decrease to a greater extent than the decrease in the transmissivity of red light 68 through the plasma outlet line 34. The difference between the transmission of green light 70 and red light 68 through the plasma outlet line 34 is indicative of the concentration of free plasma hemoglobin in the separated plasma present in the portion of the plasma outlet line 34 positioned within the optical sensor assembly 62 during the time period over which a reading is taken. Exemplary systems using red and green light to detect the presence of free plasma hemoglobin in separated plasma and determining its concentration are described in greater detail in U.S. Pat. No. 7,789,245 and U.S. patent application Ser. No. 14/577,124, both of which are hereby incorporated herein by reference. It should be understood that the present disclosure is not limited to a particular system or method for detecting the presence of free plasma hemoglobin in separated plasma and determining its concentration, but that any other suitable system and method for determining the concentration of free plasma hemoglobin in separated plasma may be employed without departing from the scope of the present disclosure According to one method of using the fluid processing system 10 and fluid flow circuit 12, a plasma-containing fluid is drawn from a fluid source into the fluid separation chamber 28 during a draw phase or mode (FIG. 5), where it is separated into concentrated fluid and separated plasma. The separated plasma is retained by the system 10 (e.g., within the separated plasma container 38 of the fluid flow circuit 12), while the concentrated fluid is returned to a fluid recipient during a return or reinfusion phase or mode (FIG. 6). In one embodiment, the draw and return phases are repeatedly alternated (drawing from the fluid source, separating the fluid into plasma and concentrated fluid, and then returning the concentrated fluid to the fluid recipient) until a target (e.g., a collected amount of separated plasma) is achieved. All of the draw phases and all of the return phases may be identical or may differ from each other. For example, a final draw phase may draw less fluid from the fluid source than the previous draw phases and a final return phase may infuse a combination of concentrated fluid and replacement fluid to the fluid recipient, whereas the previous return phases return only concentrated fluid to the fluid recipient.

Figure 7:
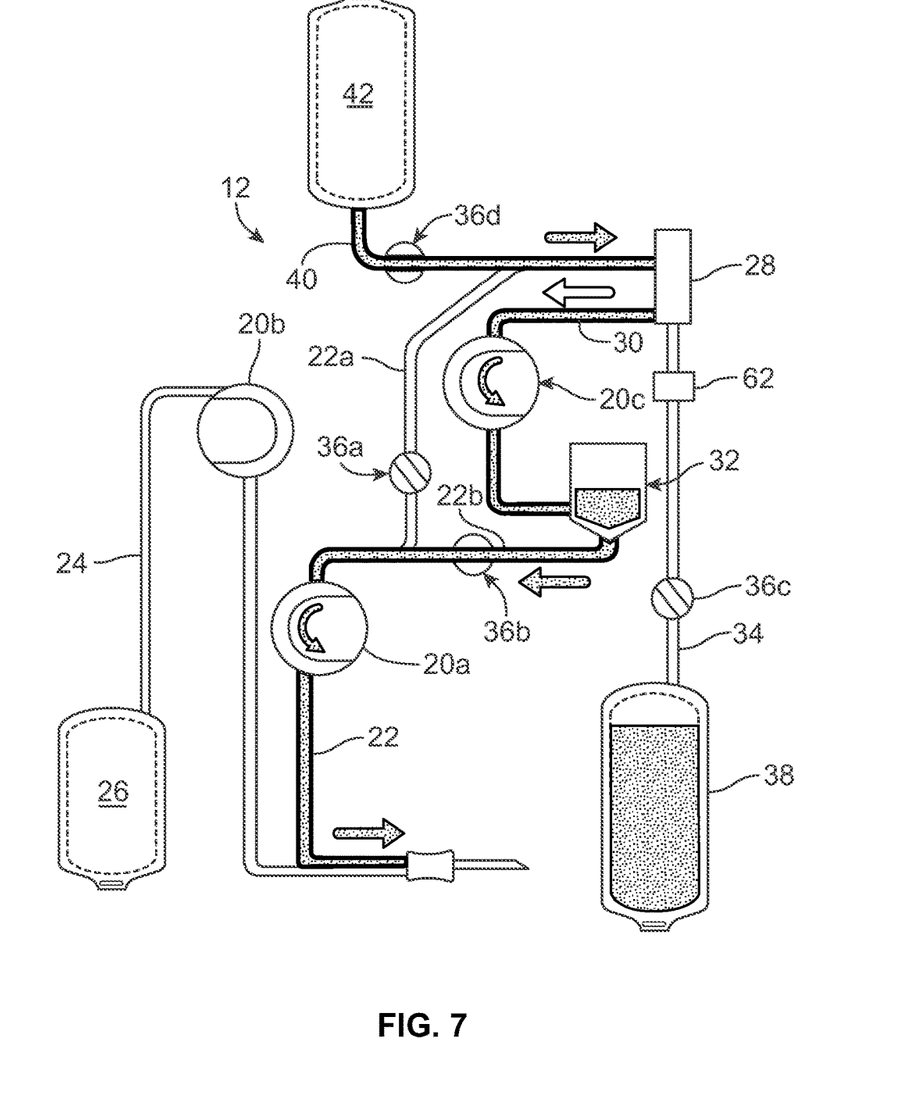
FIG. 7 is a schematic view of the fluid flow circuit and fluid processing system of FIG. 3, in a replacement fluid return mode.

FIG. 7 shows an exemplary phase or mode in which replacement fluid (e.g., saline) is directed to the fluid recipient, either alone or with an amount of concentrated fluid. In the phase of FIG. 7, the clamp or valve 36*d* associated with the replacement fluid line 40 is opened to allow replacement fluid to flow out of the replacement fluid source 42. The clamp or valve 36*a* associated with the draw branch 22*a* of the source/recipient access line 22 may be in a closed condition to prevent fluid flow therethrough, such that the replacement fluid is directed into the fluid separation chamber 28. The replacement fluid is pulled out of the fluid separation chamber 28 and into the concentrated fluid reservoir 32 by operation of the pump 20*c* associated with the concentrated fluid outlet line 30. If there is any concentrated fluid in the concentrated fluid reservoir 32, then the replacement fluid mixes with the concentrated fluid prior to being pumped to the fluid recipient by the pump 20*a* associated with the source/recipient access line 22, otherwise the replacement fluid alone may be pumped to the fluid recipient. In one embodiment, the replacement fluid return mode of FIG. 7 is carried out only once, as a final return phase (e.g., when the amount of concentrated fluid in the concentrated fluid reservoir 32 is at a sufficiently low level) in which a mixture of concentrated fluid and replacement fluid is returned to the fluid recipient. This may be advantageous to ensure that all of the concentrated fluid in the concentrated fluid reservoir 32 (along with any remaining in the fluid separation chamber 28) is rinsed out of the concentrated fluid reservoir 32 and pumped to the fluid recipient.

In other embodiments, the replacement fluid return mode of FIG. 7 may be carried out at other times, such as earlier in the procedure, at multiple scheduled times during a procedure, and/or at any time upon a request from the operator and/or using a different path between the replacement fluid source 42 and the fluid recipient. For example, it may be advantageous for the replacement fluid to bypass the fluid separation chamber 28 and the concentrated fluid reservoir 32 if the replacement fluid is being pumped to a fluid recipient earlier in the procedure. In this case, the clamp or valve 36*d* associated with the replacement fluid line 40 and the clamp or valve 36*a* associated with the draw branch 22*a* of the source/recipient access line 22 may be opened to allow fluid flow therethrough, with the clamp or valve 36*b* associated with the reinfusion branch 22*b* in a closed condition to prevent fluid flow therethrough. The pump 20*a* associated with the source/recipient access line 22 may be activated (with the other two pumps 20*b* and 20*c* inactive) to draw replacement fluid out of the replacement fluid source 42 and through the replacement fluid line 40, the draw branch 22*a*, and finally the source/recipient access line 22 to the fluid recipient.

Prior to using the system 10 for a fluid separation procedure, it may be advantageous to ensure that the fluid flow circuit 12 has been properly mounted onto or otherwise associated with the system 10 (as is FIG. 3). The system controller 16 may take any of a number of actions as part of an "install check" stage or phase that is carried out after the fluid flow circuit 12 has been associated with the system 10, but before processing begins. For example, the system 10 may use one or more weight scales and/or pressure sensors to ensure that a new fluid flow circuit 12 has been installed (to avoid a previously used fluid flow circuit 12 being left on the system 10 between uses) and that the fluid flow circuit 12 is not defective (e.g., ensuring that it has no leaks or faulty seals).

According to one aspect of the present disclosure, the optical sensor assembly 62 associated with the plasma outlet line 34 may be used to ensure that the plasma outlet line 34 is properly received by the optical sensor assembly 62, as in FIGS. 3 and 9. Briefly stated, the presence of a portion of the plasma outlet line 34 in the optical sensor assembly 62 will prevent a certain amount of light 68, 70 from the light source 64 from reaching the light detector 66. Thus, if the amount of light 68, 70 received by the light detector 66 is not sufficiently low (i.e., not equal to or below a certain level), then it may be concluded that the plasma outlet line 34 is not properly associated with the optical sensor assembly 62. On the other hand, if the amount of light 68, 70 received by the light detector 66 is sufficiently low, then it may be concluded that something (understood to be a portion of the plasma outlet line 34) is properly received by the optical sensor assembly 62. It should be understood that this aspect of the present disclosure is not limited to monitoring the installation of the plasma outlet line 34, but may be employed for any other component of the fluid flow circuit 12 (including tubing or a container) that has a portion received by an optical sensor assembly.

More particularly, as described above, the light detector 66 of the optical sensor assembly 62 is associated with the system controller 16 in a way that allows the light detector 66 to transmit an output to the controller 16 that is indicative of the amount of light from the light source 64 being received by the light detector 66. A certain amount of light 68, 70 from the light source 64 will be received by the light detector 66 when the optical sensor assembly 62 is empty (i.e., before the plasma outlet line 34 has been installed, as in FIG. 8). The light detector 66 may generate an output that is received by the controller 16 and stored as a baseline value, which is indicative of the amount of light 68, 70 from the light source 64 that the light detector 66 receives when the optical sensor assembly 62 is empty. If provided, a reference detector 76 may also generate an output that is considered when determining whether tubing has been properly installed.

The baseline value may be generated and stored during a "pre-install" stage or phase each time that the system 10 is used or may be generated and stored less frequently. If a new baseline value is not generated and stored each time that the system 10 is used, then it may be advantageous for the optical sensor assembly 62 to include a reference detector 76 (as in the illustrated embodiment), which may transmit a signal or output to the controller 16 that allows the baseline value to be adjusted for any difference in the amounts of light 68, 70 emitted by the light source 64 at the time that the baseline value was stored and the time at which the controller 16 checks whether the plasma outlet line 34 has been properly associated with the optical sensor assembly 62. For example, if the output generated by the reference detector 76 indicates that the light source 64 is currently emitting light 68, 70 at a level that is approximately 98% of the amount of light 68, 70 emitted at the time that the baseline value was stored, then the controller 16 may adjust the baseline value (e.g., by multiplying it by 0.98).

Just as a certain amount of light 68, 70 from the light source 64 will be received by the light detector 66 when the optical sensor assembly 62 is empty (FIG. 8), a certain amount of light 68, 70 from the light source 64 will be received by the light detector 66 when a portion of the plasma outlet line 34 is properly received by the light detector 66 (FIG. 9). The exact amount of light 68, 70 that is prevented from reaching the light detector 66 by the portion of the plasma outlet line 34 received by the optical sensor assembly 62 may vary depending on a number of factors, including (but not limited to) the nature of the light 68, 70 emitted by the light source 64 and the configuration and material composition of the portion of the plasma outlet line 34 positioned within the optical sensor assembly 62. In one example ("Example 1"), it was found that generally translucent or transparent, flexible plastic tubing having an inner diameter of approximately 0.118" and an outer diameter of approximately 0.178" resulted in the light detector 66 receiving an average of only approximately 51.5% or approximately 59.9% or approximately 59.3% or approximately 53.7% (depending on the particular system 10 tested) of the light 68, 70 from the light source 64 that it would have received in the absence of the tubing. Thus, based on this example, when the light detector 66 generates an output that is less than approximately 60% of the baseline value (which indicates that the light detector 66 has received approximately 60% or less of the light 68, 70 from the light source 64 that it would have received in the absence of tubing within the optical sensor assembly 62), then it may be said that the output is indicative of the tubing having been properly installed within the optical sensor assembly 62.

In another example ("Example 2"), opaque tubing having the same inner and outer diameter as in Example 1 was tested. In Example 2, the opaque tubing resulted in the light detector 66 receiving an average of only approximately 36.3% or approximately 39.2% (depending on the particular system 10 tested) of the light 68, 70 from the light source 64 that it would have received in the absence of the tubing. In another example ("Example 3"), generally translucent or transparent, flexible plastic tubing having an inner diameter of approximately 0.039" and an outer diameter of approximately 0.079" was tested. In Example 3, the "low ID" tubing resulted in the light detector 66 receiving an average of only approximately 52.1% or approximately 60.0% or approximately 62.4% or approximately 52.7% (depending on the particular system 10 tested) of the light 68, 70 from the light source 64 that it would have received in the absence of the tubing. In yet another example ("Example 4"), generally translucent or transparent, flexible plastic tubing having an inner diameter of approximately 0.120" and an outer diameter of approximately 0.176" was tested. In Example 4, the "thin wall" tubing resulted in the light detector 66 receiving an average of only approximately 55.3% or approximately 52.1% or approximately 53.5% (depending on the particular system 10 tested) of the light 68, 70 from the light source 64 that it would have received in the absence of the tubing. Thus, in any of Examples 1-4, an output less than or equal to approximately 62.4% of the baseline value would indicate that tubing has been properly installed within the optical sensor assembly 62.

The controller 16 may compare the output from the light detector 66 at the time that the optical sensor assembly 62 is empty (i.e., the baseline value) to the output from the light detector 66 at the time when a portion of the plasma outlet line 34 should be received by the optical sensor assembly 62 (a "verification output"). If the verification output is equal to or less than a selected percentage of the baseline value, then the controller 16 may consider the plasma outlet line 34 to be properly received by the optical sensor assembly 62 because something (understood to be the portion of the plasma outlet line 34 received within the optical sensor assembly 62) is preventing at least as much light 68, 70 from reaching the light detector 66 as would be prevented by the presence a plasma outlet line 34 that has been properly associated with the optical sensor assembly 62. On the other hand, if the verification output is greater than the selected percentage of the baseline value, then the controller 16 may consider the plasma outlet line 34 to not be properly received by the optical sensor assembly 62 because there has not been the expected reduction in the amount of light 68, 70 received by the light detector 66 at the time that the verification output is generated. For example, if the verification output is equal to or greater than the baseline value, then it is likely that the plasma outlet line 34 has not been installed within the optical sensor assembly 62 or that tubing was present in the optical sensor assembly 62 at the time that the baseline value was stored and either remains present (if the verification output is equal to the baseline value) or has since been removed (if the verification output is greater than the baseline value). If the verification output is greater than the selected percentage of the baseline value, then the controller 16 may generate an alert or alarm condition to notify an operator that there is a possible error in the way in which the plasma outlet line 34 was installed within the optical sensor assembly 62.

As described above, based on Examples 1-4, 62.4% may be an appropriate selected percentage of the baseline value to compare against the verification output. However, it is also within the scope of the present disclosure for the selected percentage to be some other value. For example, due to structural differences in the plasma outlet line 34 resulting from variations in the manufacturing process (which may cause a particular tubing specimen to allow a relatively high amount of light 68, 70 to reach the light detector 66), it may be advantageous to use a relatively high selected percentage (e.g., a value that is 2-3 standard deviations above the mean experimental value). In one embodiment, the selected percentage may be approximately midway between the baseline value and the experimentally determined percentage of light 68, 70 that reaches the light detector 66 in the presence of tubing. For example, for the tubing tested in the above Example 1, it was determined that a verification output of 60% or less is indicative of properly installed tubing. Thus, using a selected percentage approximately midway between the baseline value (100%) and the experimentally determined percentage (60%) would mean that selected percentage of approximately 80% (such as exactly 80%) is used when comparing the verification output to the baseline value.

Conversely, if the verification output is too low, then it may be indicative of an error in the tubing or in the way that the tubing has been installed or in the way in which the optical sensor assembly 62 is operating. Accordingly, it is also within the scope of the present disclosure for the controller 16 to, at the same time that it compares the verification output to the baseline value, compare the verification output to a preselected minimum value. In this case, the controller 16 would seek to confirm that the verification output is within a particular range (i.e., less than a particular percentage of the baseline value to confirm that tubing has been installed and greater than another particular percentage of the baseline value to confirm that there is no other error, such as the presence of plasma or other fluid in the tubing). For example, in the above Example 1, the lowest percentage of light 68, 70 transmitted through properly installed tubing was approximately 51.5% of the baseline value, in which case the preselected minimum value could be anything less than 51.5% (e.g., 50% of the baseline value).

If the controller 16 finds the verification output to be outside of the specified range, then it may generate an alarm or alert condition, which may differ depending on whether the verification output is above or below the specified range. For example, following an alarm or alert condition, an operator may be allowed to make adjustments to the way in which the fluid flow circuit 12 is mounted onto the system 10. After the operator has adjusted the fluid flow circuit 12, the system 10 may again compare a verification output to a baseline value to determine whether the fluid flow circuit 12 has been properly installed. In another embodiment, the system 10 may end the procedure (optionally powering off) and require the operator to reinitiate the procedure.

Certain corrections or adjustments may be made when generating a baseline value and a verification output. For example, in one embodiment, the baseline value and the verification output represent transmission levels, which are indicative of the amount of light from the light source 64 that is received by the light detector 66, but factor in various corrections and adjustments to a raw signal (e.g., to account for background or environmental light received by the light detector 66). Thus, it should be understood that it is within the scope of the present disclosure for the baseline value and for the verification output to be indicative of the amount of received light without being strictly equal to the amount of received light.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fluid processing system configured to cooperate with a fluid flow circuit, the fluid processing system comprising:
    an optical sensor assembly configured to receive a portion of the fluid flow circuit and comprising
        a light source configured to emit a light, and
        a light detector configured to receive a portion of the light emitted by the light source and to produce an output indicative of the amount of received light; and
    a controller configured to receive the output from the light detector and to determine
        whether said portion of the fluid flow circuit is properly received by the optical sensor assembly by
            comparing the output from the light detector to a baseline value that is indicative of the amount of light from the light source that is received by the light detector in an absence of said portion of the fluid flow circuit,
            determining that said portion of the fluid flow circuit is not properly received by the optical sensor assembly when the output from the light detector is greater than a selected percentage of the baseline value, and
            determining that said portion of the fluid flow circuit is properly received by the optical sensor assembly when the output from the light detector is equal to or less than said selected percentage of the baseline value, and
        a characteristic of a fluid flowing through said portion of the fluid flow circuit using said light.

2. The fluid processing system of claim 1, wherein the fluid processing system is configured as a fluid separation system for separating a plasma-containing fluid into separated plasma and a concentrated fluid.

3. The fluid processing system of claim 2, wherein said portion of the fluid flow circuit comprises tubing.

4. The fluid processing system of claim 3, wherein said tubing comprises a portion of a plasma outlet line associated with a fluid separation chamber of the fluid flow circuit.

5. The fluid processing system of claim 1, wherein said selected percentage is approximately midway between the baseline value and an experimentally determined output that is indicative of the amount of light from the light source that is received by the light detector when said portion of the fluid flow circuit is properly received by the optical sensor assembly.

6. The fluid processing system of claim 1, wherein said selected percentage is between approximately two to three standard deviations above an experimentally determined average output that is indicative of the amount of light from the light source that is received by the light detector when said portion of the fluid flow circuit is properly received by the optical sensor assembly.

7. The fluid processing system of claim 1, wherein said selected percentage is approximately 80%.

8. The fluid processing system of claim 1, wherein the light source comprises a light-emitting diode.

9. The fluid processing system of claim 1, wherein the light source comprises a bi-color light-emitting diode.

10. The fluid processing system of claim 1, wherein the light source is configured to emit a red light.

11. The fluid processing system of claim 1, wherein the light source is configured to emit a green light.

12. A method of determining whether a portion of a fluid flow circuit is properly associated with a fluid processing system, comprising:
   emitting a light through a space configured to receive a portion of a fluid flow circuit;
   receiving at least a portion of the light;
   comparing the amount of received light to a baseline value that is indicative of the amount of light received in an absence of said portion of the fluid flow circuit;
   determining that the portion of the fluid flow circuit is not properly associated with the fluid processing system when the amount of received light is greater than a selected percentage of the baseline value;
   determining that the portion of the fluid flow circuit is properly associated with the fluid processing system when the amount of received light is equal to or less than said selected percentage of the baseline value; and
   upon determining that the portion of the fluid flow circuit is properly associated with the fluid processing system, determining a characteristic of a fluid flowing through the portion of the fluid flow circuit using the light.

13. The method of claim 12, wherein said portion of a fluid flow circuit comprises tubing.

14. The method of claim 13, wherein said tubing comprises a portion of a plasma outlet line associated with a fluid separation chamber of the fluid flow circuit.

15. The method of claim 12, wherein said selected percentage is approximately midway between the baseline value and an experimentally determined output that is indicative of the amount of light received when said portion of the fluid flow circuit is properly associated with the fluid processing system.

16. The method of claim 12, wherein said selected percentage is between approximately two to three standard deviations above an experimentally determined average output that is indicative of the amount of light received when said portion of the fluid flow circuit is properly associated with the fluid processing system.

17. The method of claim 12, wherein said selected percentage is approximately 80%.

18. The method of claim 12, further comprising generating said baseline value by
   emitting said light through said space when said space is empty;
   receiving at least a portion of the light passing through said empty space; and
   recording the amount of light received after passing through said empty space as said baseline value.

19. The method of claim 12, wherein said emitting a light includes emitting a red light.

20. The method of claim 12, wherein said emitting a light includes emitting a green light.

* * * * *